(12) United States Patent
Flinchbaugh

(10) Patent No.: US 6,673,051 B2
(45) Date of Patent: Jan. 6, 2004

(54) MAGNETIC VALVE BLADDER CYCLER DRAINAGE SYSTEM AND USE METHOD WITH URINARY CATHETERS

(75) Inventor: David E. Flinchbaugh, Orlando, FL (US)

(73) Assignee: Hook Research Foundation, Panama City (PA)

( * ) Notice: Subject to any disclaimer, the term of this patent is extended or adjusted under 35 U.S.C. 154(b) by 47 days.

(21) Appl. No.: 10/010,534

(22) Filed: Dec. 7, 2001

(65) Prior Publication Data

US 2002/0143318 A1 Oct. 3, 2002

Related U.S. Application Data

(60) Provisional application No. 60/280,767, filed on Apr. 2, 2001, provisional application No. 60/280,768, filed on Apr. 2, 2001, and provisional application No. 60/324,601, filed on Sep. 25, 2001.

(51) Int. Cl.⁷ .................................................. A61M 5/00
(52) U.S. Cl. ..................................................... 604/247
(58) Field of Search ................................. 604/907, 908, 604/912, 915, 919, 920, 65–67, 96, 99, 101–109, 177, 265, 328, 544, 323, 256, 253, 248–251, 247, 246, 245, 93; 251/65

(56) References Cited

U.S. PATENT DOCUMENTS

| 3,642,004 A | * | 2/1972 | Oshagen et al. ........ 128/349 R |
| 3,777,737 A | * | 12/1973 | Bucalo ........................... 128/1 |
| 4,230,102 A | | 10/1980 | Ekbladh ..................... 606/192 |
| 4,424,058 A | | 1/1984 | Parsons et al. ............. 604/118 |
| 4,865,588 A | * | 9/1989 | Flinchbaugh ............... 604/129 |
| 4,869,457 A | * | 9/1989 | Ewerlof ......................... 251/6 |
| 4,994,020 A | * | 2/1991 | Polyak ........................ 600/31 |
| 5,011,472 A | * | 4/1991 | Aebischer et al. ............ 604/50 |
| 5,030,199 A | * | 7/1991 | Barwick et al. .............. 600/29 |
| 5,041,092 A | * | 8/1991 | Barwick ..................... 604/104 |
| 5,114,412 A | | 5/1992 | Flinchbaugh ............... 604/247 |
| 5,445,613 A | * | 8/1995 | Orth ............................ 604/66 |
| 6,066,088 A | * | 5/2000 | Davis .......................... 600/29 |
| 6,106,503 A | * | 8/2000 | Pfeiderer et al. ........... 604/246 |

* cited by examiner

*Primary Examiner*—Weilun Lo
*Assistant Examiner*—Michael G. Bogart

(57) ABSTRACT

A low-pressure fluid flow control magnetic valve (cycler) device, system and method for use emptying the contents of bladder by a catheter. The device can be connected with a specified drainage tubing to function as a hydrodynamically balanced system (to empty into a typical two-liter collection bag). The cycler can be connected externally to a urinary catheter for hospital, clinical and home-care use for the emptying of the bladder of a patient through a catheter in a biologically more natural, filling and draining, cyclic manner. Fully automatic, modes of operation are provided for opening and closing this valve to empty the bladder of urine when appropriate or necessary. The modes of operation respond to normal human (or animal) body pressures, or are automatic with a manual override. This device is U.S.F.D.A. approved for human use and responds to normal human (or animal) body pressures to assist the detrusor muscle to function normally in spite of an indwelling catheter challenge. The cycler device avoids problems with bladder atone, bladder spasms, harmful struvite crystal formation, bladder retraining after surgery, and allowing urine tract washout to occur as the body's primary defense mechanism against urinary tract infections.

13 Claims, 9 Drawing Sheets

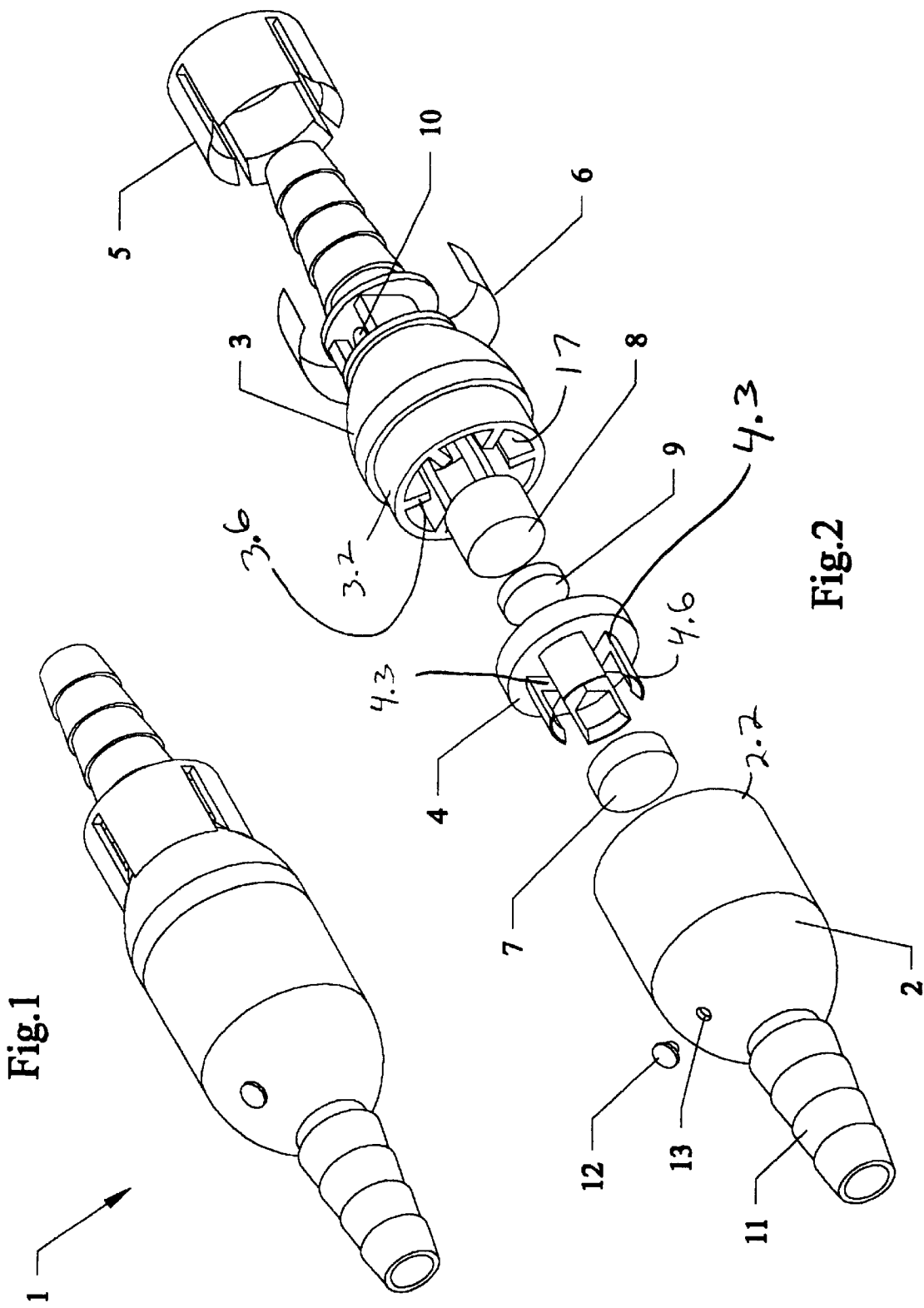

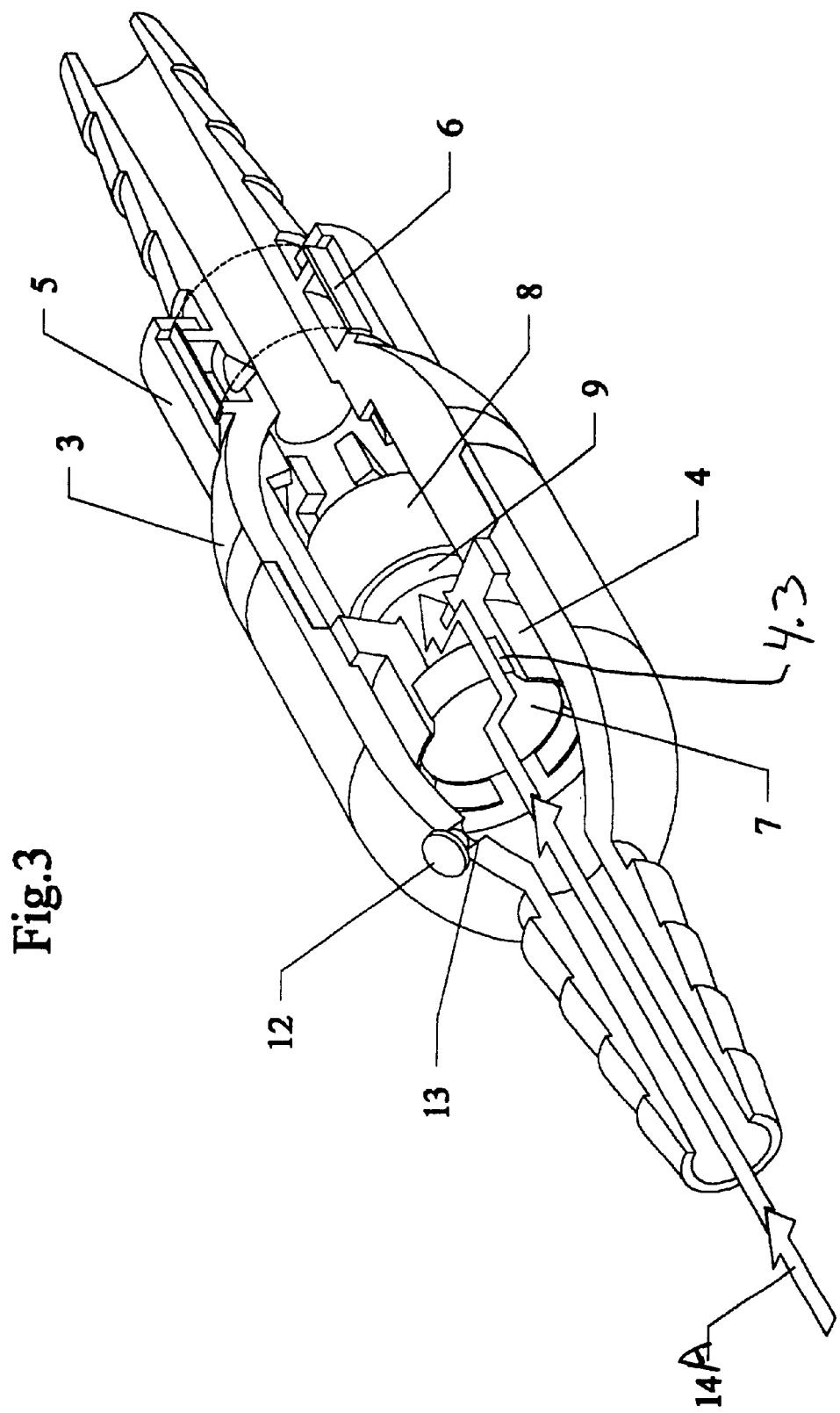

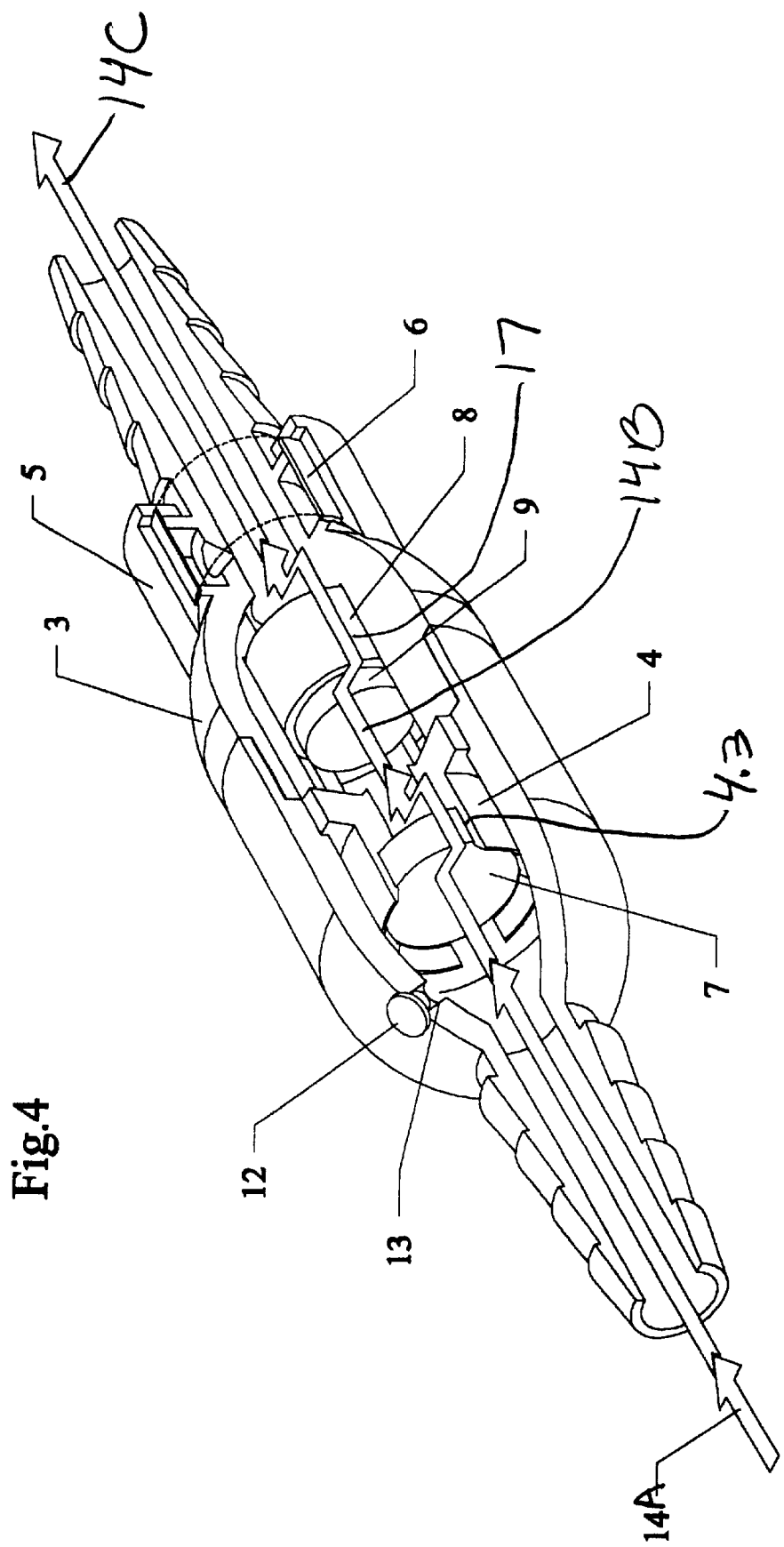

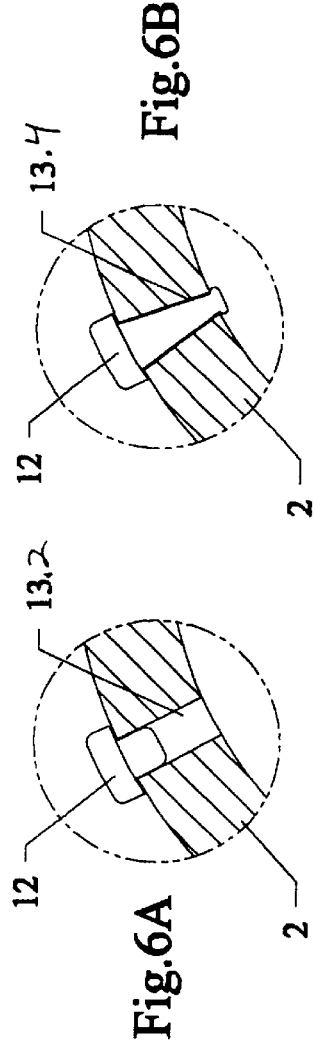
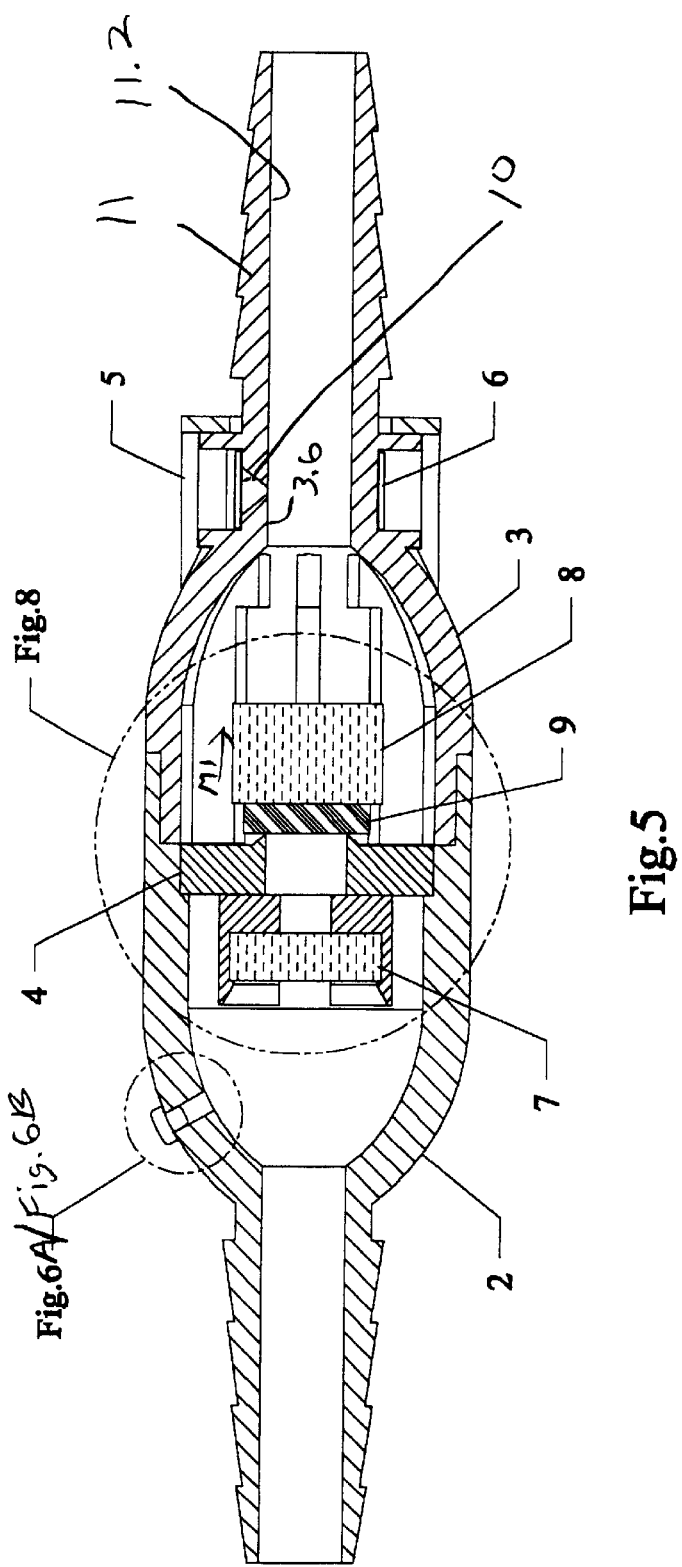
Fig.6A  Fig.6B
Fig.8
Fig.5

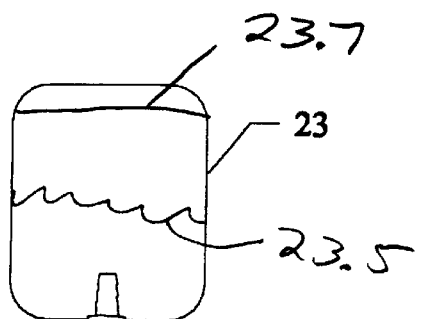
Fig. 10
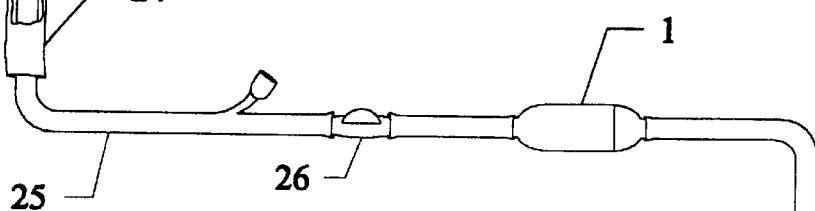
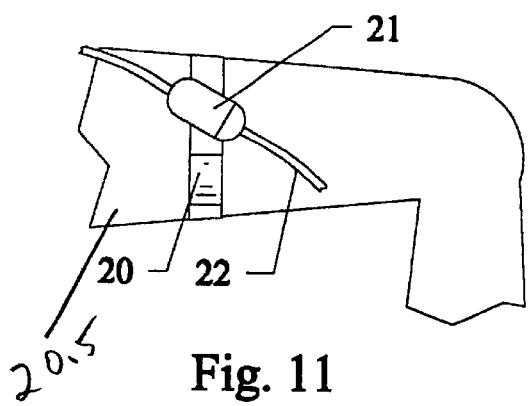
Fig. 11
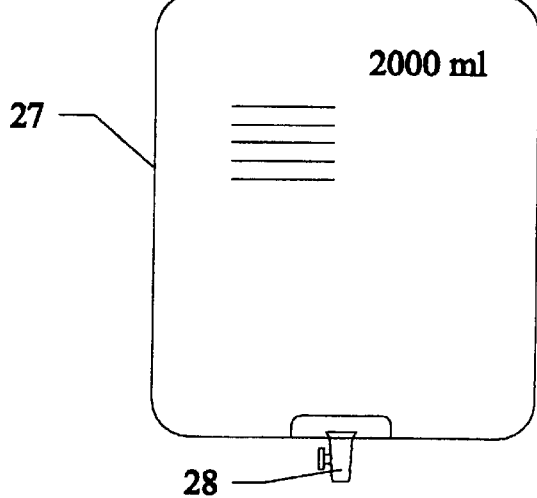

MAGNETIC VALVE BLADDER CYCLER DRAINAGE SYSTEM AND USE METHOD WITH URINARY CATHETERS

This invention relates to urinary catheters, and in particular to a method and apparatus for a pressure-activated, magnetic-force-controlled human (or animal) bladder drainage cycling valve system(Uro Cycler), for restoring normal body functions of bladder filling and emptying in cyclic manners of catheterized patients, and this invention claims the benefit of priority to U.S. Provisional Application No. 60/280,767, filed Apr. 2, 2001, U.S. Provisional Application No. 60/280,768 filed Apr. 2, 2001, and U.S. Provisional Application No. 60/324,601 filed Sep. 25, 2001.

BACKGROUND AND PRIOR ART

Urinary catheters bypass the normal bladder process of storing urine, and only releasing the urine by using the bladder detrusor muscle. Catheters can be a necessary tool to open the bladder to allow urination when patients have trouble urinating. A catheter can be a lifesaving tool since an uncontrolled buildup of urine can cause serious medical problems including death. However, there are known problems with catheters.

Struvite crystal encrustation is the effect of stagnated urine in the neck of the bladder when using a catheter. In the face of an indwelling catheter, urine can pool at the neck of the bladder, and the pooled urine can shift from a normal pH factor to an abnormal pH level of 10 or more while it stagnates. Urine shifts to an ammonia state where struvite crystals can precipitate and enlarge on the indwelling catheter. This situation can occur as the bladder loses its natural ability to cyclically flush itself in the face of an indwelling catheter. Bladder wall thickening has also be observed in long-term catheterizations and may be a result of the increasing pH levels.

Urinary tract infections can occur as the urine stagnates and shifts from its normal, acidic antibiotic property through the pH spectrum. Pooled urine that can occur in the neck of the bladder beneath the indwelling catheter can be a natural breeding ground for microbes which can migrate in the body.

Bladder spasms can also occur with an indwelling catheter which causes the bladder to cease its normal cycle of filling and flushing. A dynamic functioning system is converted to a static state with a catheter, and painful bladder spasms can occur. Bladder atone can also occur where short term or more permanent loss of natural bladder functions occurs by using a catheter.

It is also generally well known in medical circles that a human bodies primary defense mechanism against urinary track infections and the other problems listed above is the process known as "wash-out", where it is advantageous to allow a bladder to normally fill up and be released at one time rather than in an uncontrolled drip fashion that would occur with using a catheter.

Various catheter type instruments and procedures have been used for draining bladders of patients in hospitals. These instruments and procedures have evolved from constant (non-cycling) drip drainage through painfully inserted catheters by siphoning, suction and various types of awkward manually externally controlled cycling apparatus and procedures. Fundamental to an effective, safe, and appropriate device and method is allowing the bladder to fill reasonably and then draining it without a suction pump and without allowing build-up or entry of infectious contaminants in the drainage system.

Included in previous methods and devices have been U.S Pat. Nos. 2,602,448 and 2,860,636 which utilized a siphon in combination with a reservoir to provide cyclic draining of the bladder. Pressure release in these devices is controlled by raising the height of the device on a bedside tree. It is subject to distortion by shifting and turning of the patient and is unreliable (and can compromise safety) besides restricting the patient.

U.S. Pat. No. 3,598,124, describes a siphon leg controlled by merely attaching a catheter to a bedside tree at predetermined adjusted height, which varies the pressure at which the bladder will drain and provides a flutter valve near the patient to break the siphon action of the system once the bladder has drained.

U.S. Pat. No. 4,230,102, describes a device for the draining of a bladder in which a T-joint has been placed on a catheter and has a pressure membrane attached thereto in a large casing for actuating a pressure switch which in turn actuates an electric motor driving a gear train and cam. A cam follower is spring loaded to clamp the catheter for two minute cycles upon actuation by the pressure switch to drain the bladder. However, this type of device, can be expensive and bulky and positions an electrical apparatus adjacent to the catheter.

U.S. Pat. No. 4,424,058, describes a spring-return valve in conjunction with a siphon-release orifice to prevent excessive suction and to prevent urine from remaining in the system after drainage. A problem with this system was that the restoring force of the spring increased with distance of travel from a closed position. This valve was very unsatisfactory because it closed again as soon as the urine fluid pressure dropped off, thus causing fluid to remain trapped in the bladder to stagnate with further elapsed time. Only a full bladder would open it, sometimes at an uncomfortably high (and potentially unsafe) pressure, and only a relatively full bladder would keep it open to allow complete drainage unless overridden by the patient bearing down heavily on the lower abdomen. Also, positioning of tubes leading from it was parallel to the leg on which it was attached and provided a situation for retention of fluid in the system.

None of the proposed patented devices and techniques described above solves all the problems with catheters that are listed above.

Unlike the problem methods and devices of the prior art, the subject invention provides both consistent magnetic opening and closing of a valve seal with decreased rather than increased closing pressure when opened. As the bladder is emptied, decreasing head pressure against the valve can keep the valve open to establish complete and sterile drainage. In addition, the successfully-tested clinical embodiment of this invention provides simple and convenient manual override, when desired, to decrease or eliminate totally the magnetic closing pressure of the valve.

SUMMARY OF THE INVENTION

A primary objective of the invention is to provide a low pressure magnetic valve for bladder management cyclic flow control having consistent opening and closing of the valve seal with decreasing head pressure against the valve as opposed to increasing pressure. As long as any fluid is coming through the line, the valve will remain open until a complete emptying of the bladder is achieved.

A secondary objective of the invention is to provide a low pressure magnetic valve for bladder management cyclic flow control that establishes complete and sterile drainage as the bladder is being emptied.

A third objective of the invention is to provide a low pressure magnetic valve for bladder management cyclic flow control that can be automatically run with a simple and convenient manual override that can be selectively engaged.

A fourth objective of the invention is to provide a low pressure magnetic valve for bladder management cyclic flow control that helps restore normal body functions of bladder filling and emptying in a cyclic manner, with normal, healthy pressure sensations in spite of the presence of the catheter which typically inhibits "natural" bladder drainage.

The fifth objective of the invention is to provide a low pressure magnetic valve for bladder management cyclic flow control for use with a catheter which can reduce and eliminate known problems that occur with using a catheter such as urinary tract infections, struvite crystal encrustation, bladder spasms and bladder atone.

The sixth objective of the invention is to allow a user wearing a catheter to use their bladder detrusor muscle to selectively turn on a valve in the catheter and complete an entire urination emptying cycle of their bladder.

The invention provides for both consistent magnetic opening and closing of a valve seal with decreased rather than increased closing pressure when being opened. As the bladder is being emptied, the decreasing of head pressure against the valve can keep the valve open to establish a complete and sterile drainage.

In the invention, valve-closing pressure can decrease as a result of three important factors: (1) magnetic pull of a valve decreases as its open distance from magnetic attraction in the direction of the valve seat increases, (2) the gravity-enhanced fluid flow column in the drain down tube provides a slight negative pressure on the back side of the movable magnet (thus tending to hold the valve open until the drain tube empties completely), and (3) fluid passing through the system provides a partial mass flow insulation which tends to hold the moving magnet away from the fixed magnet, also decreasing the net magnetic attraction between the magnetic members. A small amount of air is allowed to leak through a micro-pore filter (which keeps out harmful micro-organisms from the closed system) in order to vent the down line for clean, dry emptying.

The very low-pressure valve system of the invention for use in controlling the flow of most fluids utilizes magnetic forces to hold a smooth surface against an ultra low-durometer (soft) composite seal or valve seat material until such time as the fluid head pressure causes the magnets to separate and the valve to open, at a preset value, to allow maximum fluid flow rate and complete drainage of the system The use method described here is medical in nature, applying to bladder drainage of catheterized patients into a urine collection bag, as needed, in a normal, cyclic fashion. In other words, head pressure of urine building up in volume against the detrusor muscle of a bladder and in a catheter running from the bladder to the valve where it is positioned on a patient's leg or rests on the bed sheet, causes the valve to open away from the valve-port seat. When the valve is opened, distance increases between the valve magnetic member and a member to which it is magnetically attracted in the direction of the valve-port wall, thereby allowing the valve to remain open with less pressure than that initially required to open it. Fluid passing between the open valve and the member to which it is attracted magnetically decreases further still the closing pressure to offset the head-pressure opening of the valve.

Downstream from the valve, there is a siphon-release air-inlet orifice that relieves siphon (negative pressure) to avoid siphon suction that would either cause collapse of the bladder walls or cause the valve to remain open after the bladder is emptied. An air inlet, allowing only air flow through a micro-pore filter material to the siphon-release orifice, is positioned upstream and radially outward from an outlet to the valve in order to prevent passage of fluid from the valve where siphon pressure does not provide sufficient inward suction of air. The siphon-release orifice is provided with an antiseptic strainer (anti-bacterial/anti-viral filter) and can serve as a low-pressure one-way inlet valve.

The entire valve system (in the embodiment of a small, streamlined, compact, integrated and durable device) also serves as an anti-reflux valve between the patient and the urine collection bag, thus preventing drained (and possibly old and unsterile, septic, contaminated) urine from ever re-entering the catheter, urethra, and bladder of the patient, and potentially causing infection or other problems.

Additional embodiments of this invention provide for a manual override of the valve by selective distancing an externally positioned magnetic member from the valve member that is attracted to it. The override gives flexibility of pressure adjustment and provides the opportunity of assuring full drainage when desired by either physician or the patient. This could manifest itself, in the event of excessive discharge of viscous matter or other mode of lumen blockage, as a "safety" valve to relieve fluid pressure buildup.

An additional swivelable attachment of the bladder cycler to a strap on a patient's leg can allow the cycler to be positioned comfortably at a slant with the outlet and tubes leading from it downward from the valve to further assure that fluid will not remain in the system between drainage cycles whether used in either a prone or vertical position of the leg. The patient also can more readily move about and not be confined or attached to the bed as long as the collection bag is kept attached for use as needed.

The invention can be used as a hospital instrument whenever an indwelling catheter is required, or in clinics, or in physician's offices, or in homes for draining urine from bladders of patients automatically and safely after normal filling, thoroughly and antiseptically. This use is in strong contrast to the typical, non-cyclical, continuous drip associated with urethral catheter drainage into a collection bag. The use of the UroCycler with catheterized patients helps restore the more normal body function of bladder filling and emptying in a cyclic manner, with normal, healthy pressure sensations in spite of the presence of the catheter which here-to-fore prevented "natural" bladder drainage.

Further objects and advantages of this invention will be apparent from the following detailed description of the presently preferred embodiments which are illustrated schematically in the accompanying drawings.

BRIEF DESCRIPTION OF THE FIGURES

FIG. 1 is a perspective view of a fully assembled, automatic drainage embodiment.

FIG. 2 is an exploded perspective view showing the components comprising this passive magnetic bladder-cycling valve.

FIG. 3 is a cutaway of the assembly showing the valve in the closed configuration FIG. 4 is a cutaway of the assembly with the valve open.

FIG. 5 is a section view of the assembly showing the valve closed.

FIGS. 6A and 6B shows an added over-pressure safety release plug embodiment.

FIG. 10 illustrates the bladder cycler being used with a connected clinician's (or physician's) self-sealing sampling port on the inlet end and a hydrodynamically-balanced outlet downline to a fluid collection bag on the outlet end.

FIG. 11 is a side view of a patient's leg with the invention strapped to it.

DESCRIPTION OF THE PREFERRED EMBODIMENTS

Figures 7A, 7B:
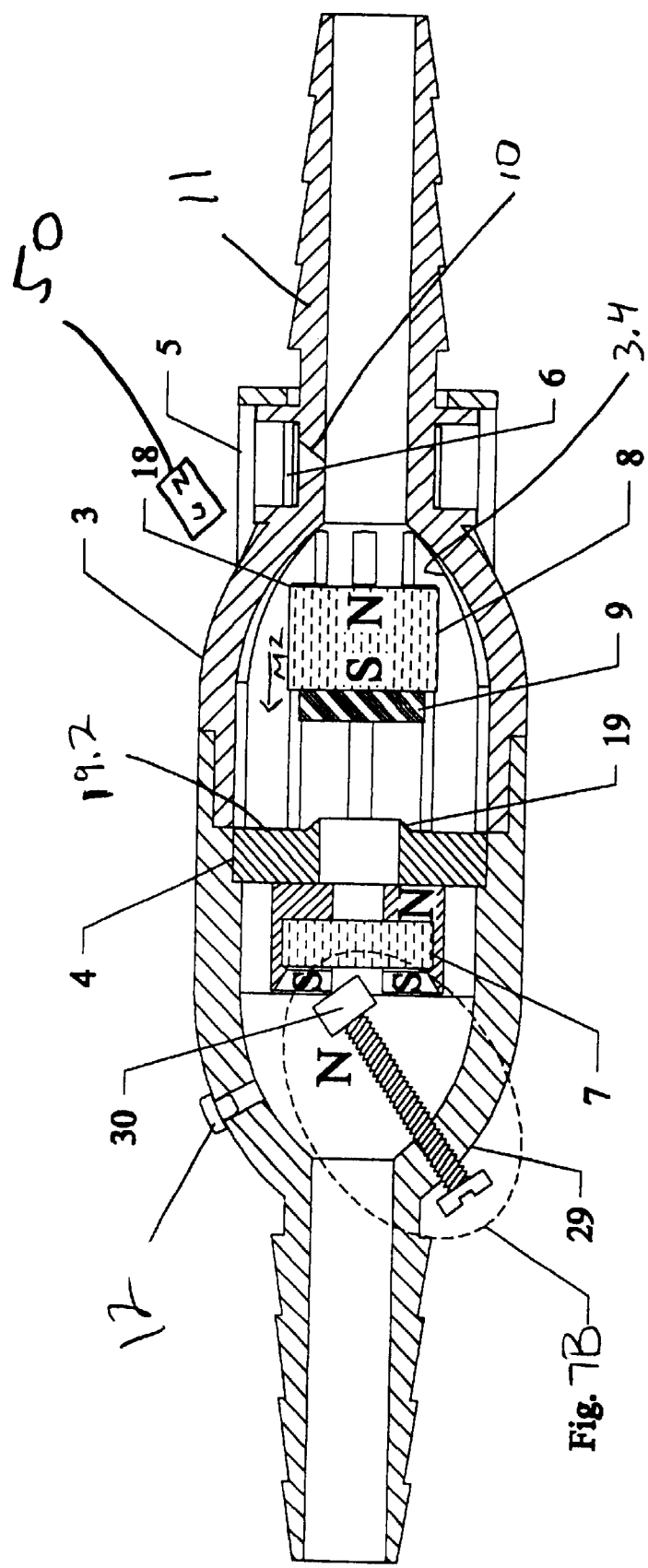
FIG. 7A is a section view of assembly with the valve open.
FIG. 7B is an enlarged view of an optional screw with magnet that can alter valve opening pressure.
Figure 7B:
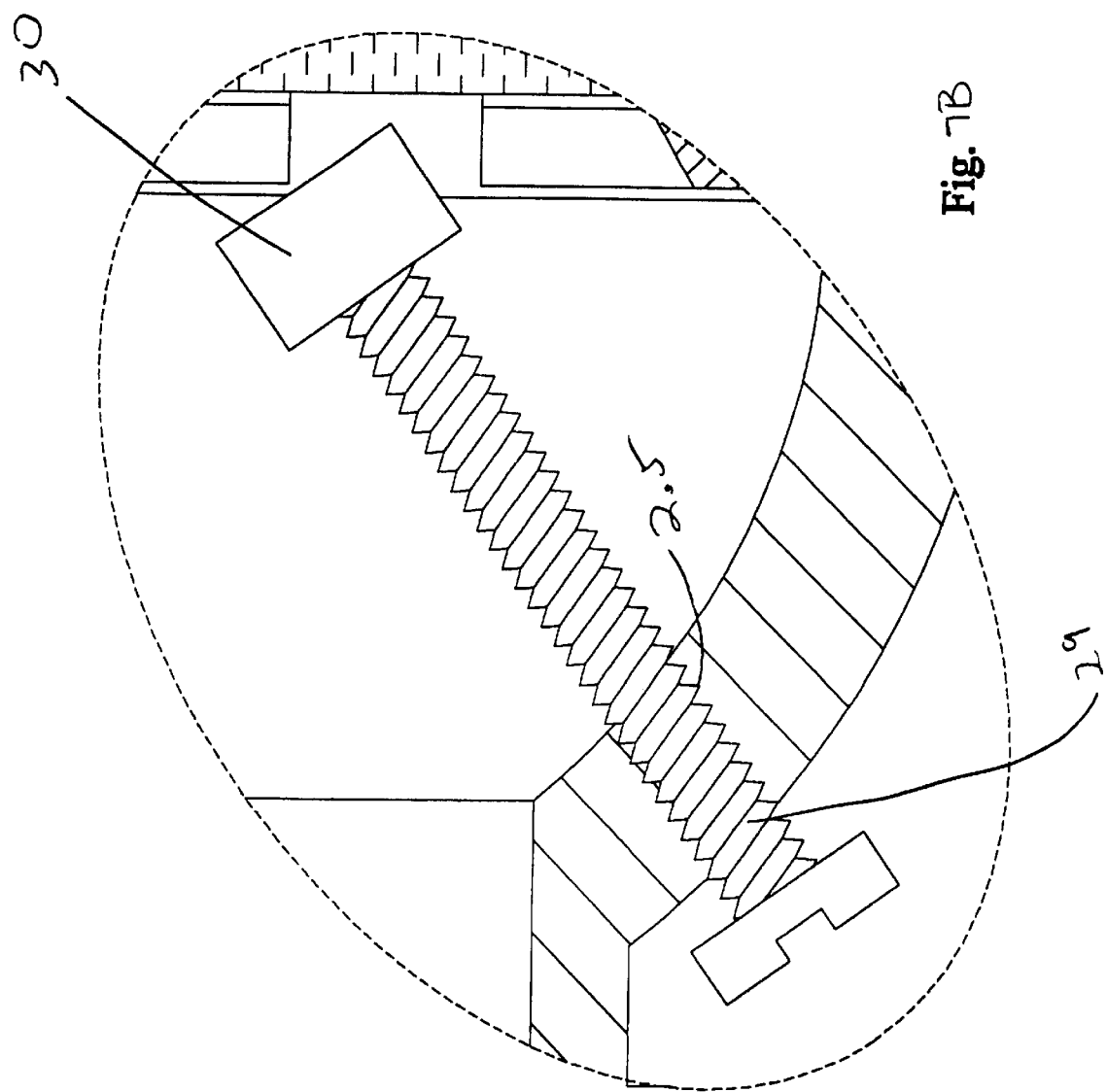

Before explaining the disclosed embodiments of the present invention in detail it is to be understood that the invention is not limited in its application to the details of the particular arrangement shown since the invention is capable of other embodiments. Also, the terminology used herein is for the purpose of description and not of limitation.

FIG. 1 is a perspective view of the fully assembled bladder cycling passive magnetic valve invention 1. FIG. 2 is an exploded view of the internal components of the invention 1 of FIG. 1. Referring to FIGS. 1 and 2, this exploded view shows the key components comprising the assembly. The inlet end, or upper non-magnetic housing 2 has female socket end 2.2 which mates with the male prong end 3.2 of outlet end, or lower housing non-magnetic 3, with a water-tight and air-tight bond. A moving magnetic valve member 8 is magnetically attracted in the direction of valve-port wall 4 where the resilient valve seal 9 contacts the valve seat at the outlet end of valve insert orifice 4. The moving magnetic valve member 8 is attracted magnetically to the valve-port wall 4 due to the fixed upstream magnetic member 7. Inwardly protruding rails 3.6 in lower housing 3 form an internal chamber for allowing the moving magnet valve 8 to slide back and forth. Fixed magnetic member 7 is held in place by prongs 4.6 extending from wall 4 having openings/slots 4.3 therebetween. The openings/slots 4.3 are large enough to allow for fluid flow around the fixed magnetic member 7. Magnetic attraction can be provided by composition of either or both the moving valve member and the upstream magnetic member. Optionally and preferably, the magnetic valve member 8 and the upstream magnetic member 7 both are inert, ceramic permanent magnets having high magnetic field saturation and high coercive magnetic force, and the valve-port wall 4 is non-magnetic. Opposite, attracting poles of each magnetic member 7, 8 are facing each other in the fully operational valve. However, when double-blind studies are conducted, a fully assembled "dummy" valve can be substituted with like magnetic poles facing each other, thus making a non-closing, constantly open, "placebo" unit. For testing purposes, a preferred embodiment of the moveable magnet member 8 was measured at approximately 130 milligauss(mG) at a distance of approximately 7 millimeters(mm) from the sensing coil of a DC Magnetometer. The fixed magnet member 7 had a measurement of approximately 40 mG. Both magnet members 7, 8 were approximately 0.375 inches in diameter. For the preferred embodiment, the pressure needed to open the valve member 8 away from its seat was adjusted to be approximately 0.1 ounces per square feet(ounces/sq.ft), which correlated to approximately 15 cm height of H2O, in the catheter line.

Referring to FIGS. 2, and 5, channel ridges 17 at the inside periphery of non-magnetic housing 3 provide fluid passage linearly between them from side-to-side of first the magnetic base member 7 and then the magnetic valve member 8.

Referring to FIGS. 5, and 7A, stopper shoulders 18 are provided to arrest travel of the magnetic valve member 8 at a select distance of travel away from valve-port wall 3.4.

Figure 8A:
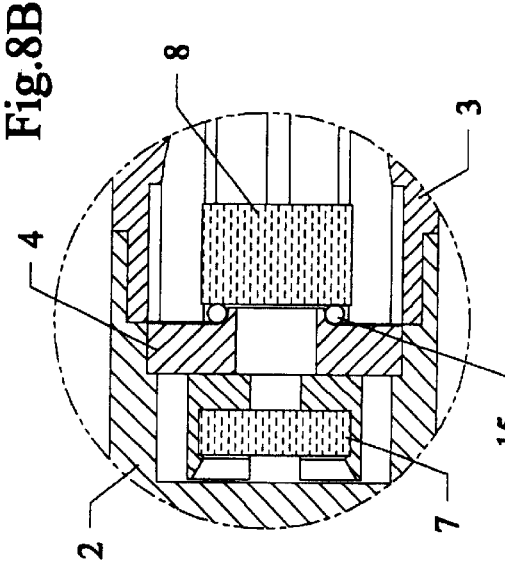
FIGS. 8A, 8B, 8C, and 8D show embodiments of valve seal and valve seat combinations and useful configurations.
Figure 8B:
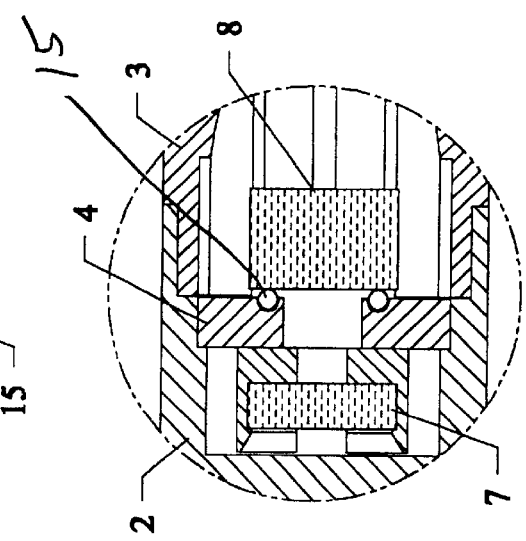
Figure 8C:
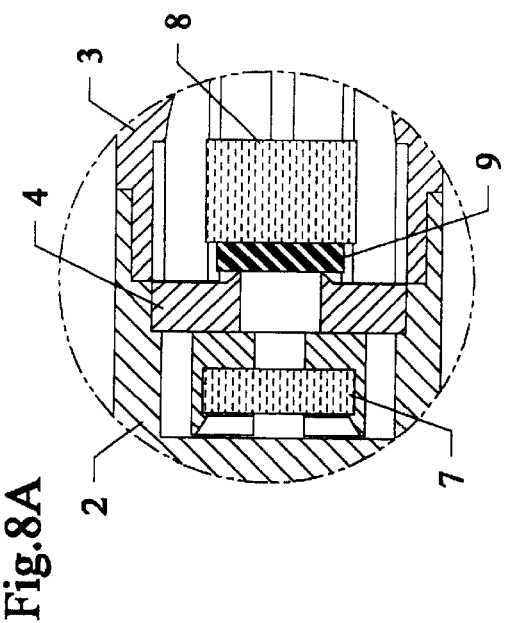
Figure 8D:
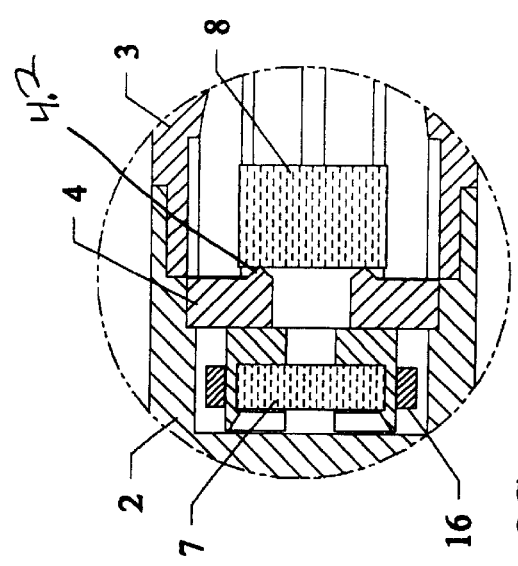

Referring to FIGS. 5, 7A and 8A–8D, the valve-port wall is provided with a valve-seat ridge 9 for reduction of valve-seat area to reduce area for accumulation of particulates in fluid passing through the system and for providing a relatively smaller surface for tightly seating into the moving valve member 8. Moving valve member 8 can move in an interior chamber within housing section 3 in both directions as shown by arrows M1 and M2. A resilient non-magnetic valve surface 9 can be provided for increased seating pressure and for selectively decreased magnetic attraction in the direction of the valve-port wall 19.2. Alternative valve seat/seal configurations are illustrated in FIGS. 8B, 8C, and 8D. In FIG. 8C, the low-durometer, soft, resilient seal 4.2 can be built into the insert 4 member and its sealing ridge 19, and a smooth surface of magnet 8 can press firmly enough to make a suitable urine flow seal. In FIGS. 8B and 8D, an FDA-approved material (eg: silicone) resilient O-ring 15 can be either bonded or inserted in the wall member of valve seat insert 4 to provide a low-pressure fluid seal against the face of the moving magnetic material 8.

Referring to FIGS. 1 through 5, and FIGS. 7A and 8A–8D, inside corners of magnetic valve member 8, inside corner edges of housing inlets 2, inside corner edges of housing outlets 3 and all other corners possible can be rounded to facilitate flow through the system and to prevent accumulation of particulates in fluid passing through the system. Outside surfaces of inlet housing 2 and outside surface of outlet housing 3 also can be rounded to prevent scraping action that would tend to accumulate particles at the outside and decrease cleanliness. In addition to being rounded, the inside corners of the housing outlets can be angled from the basically symmetrical barbed inlet and outlet connectors 11 which can be selectively tapered, ribbed or otherwise designed to receive and to hold medical tubing.

Referring to FIGS. 1 through 7B, an optional soft elastic plug 12 may be inserted into a vent line 13.2/13.4 to serve as a safety pressure release valve (perhaps if blockage in the system caused urine pressure in the bladder to build up past some potentially hazardous number like 80–120 cm/H2O column) which would pop out to avoid renal or other physiological damage. Details are shown in FIGS. 6A and 6B. In addition, this feature could allow medicine to be injected into the urinary tract on the bladder side, if desired, to control or prevent infection. FIG. 6A has a blunt edge plug 12.2, which fits within a uniform diameter vent line 13.2, and an alternative version FIG. 6B has an expanded tip 13.4 which fits within and catches against an interior surface about narrowing vent line 13.4

Referring to FIG. 7B, another (threaded) hole 2.5 could be used to position a screw 29/magnet 30 mechanism so as to position a third permanent magnet 30 in close proximity to the back of the "fixed" magnet member 7, in order to alter the net magnetic field strength and thus control the valve opening pressure. The present magnet-holding insert 4 can be molded in a soft plastic material in order to make a good seal against the moving magnet face on component 8. As shown in FIG. 7A, the South Pole of the moving magnet 8 faces the valve seat 19 at its left. This South Pole is attracted to the North Pole of the fixed magnet 7 behind the seat 19 to its left. The manual external rotational adjustment of externally adjustable screw 30 controls the magnet 30 South pole separation from the magnet 7 South pole which would allow a significant degree of valve pressure opening adjustment, or variable pressure setting, which can be desirable in certain situations. The closer magnet 30 is to magnet 7, the less net field strength there is to attract magnet 8. Conversely, when the screw 29 is backed off so that magnet 30 is farther apart from magnet 7, then magnet 30 has less effect in canceling some of the strength of magnet 7, and the opening pressure is higher. When bladder detrusor muscle atony has occurred, or when therapeutic bladder retraining is called for, lowered position of magnet 30 toward magnet 7(screwing the magnet 30 in closer), or graduated pressure settings can provide substantial additional benefits. Currently, the opening pressure setting can be determined by the insert dimensions (assuming a consistent magnet gauss reading) and each unit can acquire a fixed pressure value during the manufacturing process. While the normal opening range is approximately 15 to approximately 30 cm/H2O, individual units can be made to operate at higher or lower pressures, within practical limits.

Head pressure to open the valve can be decreased by pressing the button inwardly and sliding the magnetic base member in the direction of the housing inlet. The valve can be totally released without any magnetic pressure to hold the valve shut when the magnetic base is slid to the extreme housing-inlet end of travel of the button stem in the stem channels. Closing pressure of the valve is increased by sliding the magnetic base member in a downstream direction toward the housing outlet.

Referring to FIGS. 2, 3, 4, 5, 7A, 7B and 10 a siphon air vent micro-port filter 6 and cover 5 can be provided to effect a very low-pressure siphon, suction, or negative pressure from fluid passing through the housing outlets 11.2 and down the drain line 22 into the collection bag 27. Typically the filter material within filter 6, either woven or non-woven attaches by an adhesive and is packed around the housing vent hole 10. This feature of the invention assists in holding the valve 8 open until all the fluid is emptied out of the system as well as allowing the system tubing to drain clean and dry, thus preventing moist surfaces within the system for potential bacterial growth. The vent filter 6 allows for a stream of air bubbles to enter line 22 to aid in allowing complete drainage of all fluid through line 22, since in a gravity directed flow system an upper located vent enhances fluid flow therethrough.

Typically for construction purposes, the vent valve 10 can be positioned at the outside periphery of a valve-port wall 3.6 and the vent aperture 10 can be positioned in the outside periphery of an outlet housing member 3 that is created during plastic injection molding process or in the construction assembly process. The assembly can be either glued, chemically welded, ultrasonically welded, or press-fit snugly enough to remain assembled without glue.

Referring to FIG. 2, the magnetic base member 7 can be either glued or otherwise fixed in seats 4.6 in a position at a select distance from the valve-port wall (seat) to achieve a pre-determined pressure requirement for opening of the valve 8 in opposition to magnetic attraction of the base member 7 and the valve 8. Alternatively, however, the magnetic base member 7 in FIG. 2 can be moved by an automatic, but very weak, drainage spring or other weakly resilient member. When pressure from the weight of fluid in the bladder 23 (shown in FIG. 10) and in the column from the bladder 23 to the bladder cycler invention 1 cause the valve 8 to open in opposition to the magnetic attraction, the spring action will cause the base member 7 to move upstream away from the moving valve member 8 and thereby decrease further the attraction between the two magnets 7, 8. This allows more complete emptying of the bladder contents 23.5.

Although not manually-controllable, this invention provides some features of the controllable embodiment at a lower cost of construction. A springy material in this working relationship functions in the opposite direction as springs used to close valves in prior-art practices. It decreases rather than increases opening pressure of the valve when pressure in the bladder is low from being partially emptied. This configuration would require a very careful design and implementation in order to balance the static and dynamic forces precisely for operation, both in the opening pressure and to assure valve closing, sealing without leaking during urine pressure buildup to the opening threshold.

Referring to FIG. 10, this diagram traces out the cycler invention use method as the key component of a hydrodynamically-balanced cyclic urinary drainage system. The human (or animal) bladder 23 and bladder contents 23.5 with its two ureter inputs has its attached urethra 24 invaded by an indwelling catheter (such as a balloon-anchored Foley type) 25. On the output end, this catheter can be connected to a clinician's (physician's) sampling port 26, from which a urine sample can be drawn by either a conventional syringe needle or by a safety plastic canula probe.

Operation of using the cycler will now be described in reference to FIGS. 2, 3, 4, 5, 7A and 10. Initially, the valve 8 is in a closed position to inhibit fluid flow therethrough. Arrow 14A of FIG. 3 shows the direction of fluid flow which stops by closed seated valve 8. A patient can use their bladder detrusor muscle 23.7 about the bladder 23 to cause a small amount of pressure in the catheter line 25, 22 to cause the valve 8 in cycler 1 to pass to an open position(in the direction of arrow M1) to allow fluid flow therethrough. Arrows 14B and 14C of FIG. 4 show fluid passing through cycler 1. Fluid running down line 22 assists in maintaining the valve 8 in an open position by causing a hydrodynamic pulling on the valve 8 so that all fluid flow passes therethrough. The hydrodynamic pulling on the valve 8 causes by the fluid flowing through line 22 is stronger than the attractive forces between magnet valve 8 and member 7. After all fluid passes through line 22, no further hydrodynamic forces exist to keep the valve 8 in the open position so now valve 8 is free to move in the direction of arrow M2 to a closed position since the attractive power of the magnets 7 and 8 causes valve 8 to move in the direction of arrow M2.

Unlike using actual spring biased-backed valves used in some prior art devices, the subject invention valve 8 does not function in an equivalent manner. For example, the larger the opening of the magnetic valve 8, the less the pull(magnetic attraction with member 8) exists to close the valve 8. With a spring backed valve, the greater the opening in a valve, the greater the resistance is from the compressed spring to cause a closure of the valve. For example, a patient exerting fluid pressure to open a spring biased-backed valve has greater resistance that occurs as they try to increase urination pressure. With the subject invention magnetic valve 8, more pressure from the bladder causes less resistance against the valve 8, and helps fluid flow therethrough.

Additionally, spring biased-backed valves have been known to cause a premature closing in a catheter line which can cause any of the medical problems referred to in the background section of the invention. The subject invention magnetic valve 8 does not prematurely close since the hydrodynamic gravity enhanced pulling of fluid downline is enough to overcome the magnetic attraction to keep the valve open. When downline fluid flow ceases, the hydrodynamic gravity enhanced pulling of fluid ceases and the magnetic attraction is enough to close off valve 8.

The subject invention allows a person to use their bladder detrusor muscle to cause pressure selectively turn on and complete urination emptying cycle of the contents of the bladder while wearing a catheter.

The cycler 1 can be an alternative to using dangerous clamps on a catheter line, since clamps left on a catheter line for extended periods of time can be hazardous to a patient's life. The cycler 1 allows for a fluid samples to accumulate about port 26 so that an adequate sample can be retrieved when needed.

Referring to FIG. 10, the cycler invention 1 with magnetic moving valve 8 can be connected between the sampling port 26 and the specially-sized downline tubing 22, thus forming a hydrodynamically-balanced drainage system, terminated by the collection bag 27 and its clamped-off emptying tube 28. A preferred embodiment incorporates the connections from the catheter be made as shown, and that the downline from the outlet end of the bladder cycler valve consist of approximately 0.1875 inch inside diameter tubing, preferably of polyethylene construction. The surface tension of the watery urine fluid 23.5, combined with the lumen of the catheter and the fluid pressure, fluid flow rate, viscosity, and gravitational forces have shown that these dimensions, including the length of the drainage line, can be critical parameters for proper and safe, reliable operation as a listed Class II, U.S.F.D.A.(United States Food and Drug Administration) 510(k) medical devices. As previously described, for the preferred embodiment, the pressure needed to open the valve member 8 away from its seat was adjusted to be approximately 0.1 ounces per square feet (ounces/sq.ft), which correlated to approximately 15 cm height of H2O, in the catheter line.

Referring to FIG. 11, a leg strap 20 can be provided about a human leg 20.5 with a swivel connection 21 that allows the bladder cycler invention 1 to be positioned when desired at a downward angle with respect to a leg 20.5 to which it attached. This allows a catheter or outlet drainage tubing 22 to be positioned at a slant that provides downward flow of fluid that otherwise could remain in the system between drainage cycles.

Referring to FIGS. 9A, 9B, 9C and 9D, these graphs show the time relationship between pressure buildup on a test stand, such as in the configuration diagrammed in FIGS. 10–11, the valve opening pressure drop, the initiation of fluid flow, the constant flow rate until the point of emptying, the valve closing again, and the cycling period to the next pressure fill and open sequence. This period is normally approximately two to approximately four hours for the average adult, depending on amount of fluid beverages consumed, physical activity, and physiological factors such as bladder size, general health, pressure sensitivity, and the like.

Figure 9:
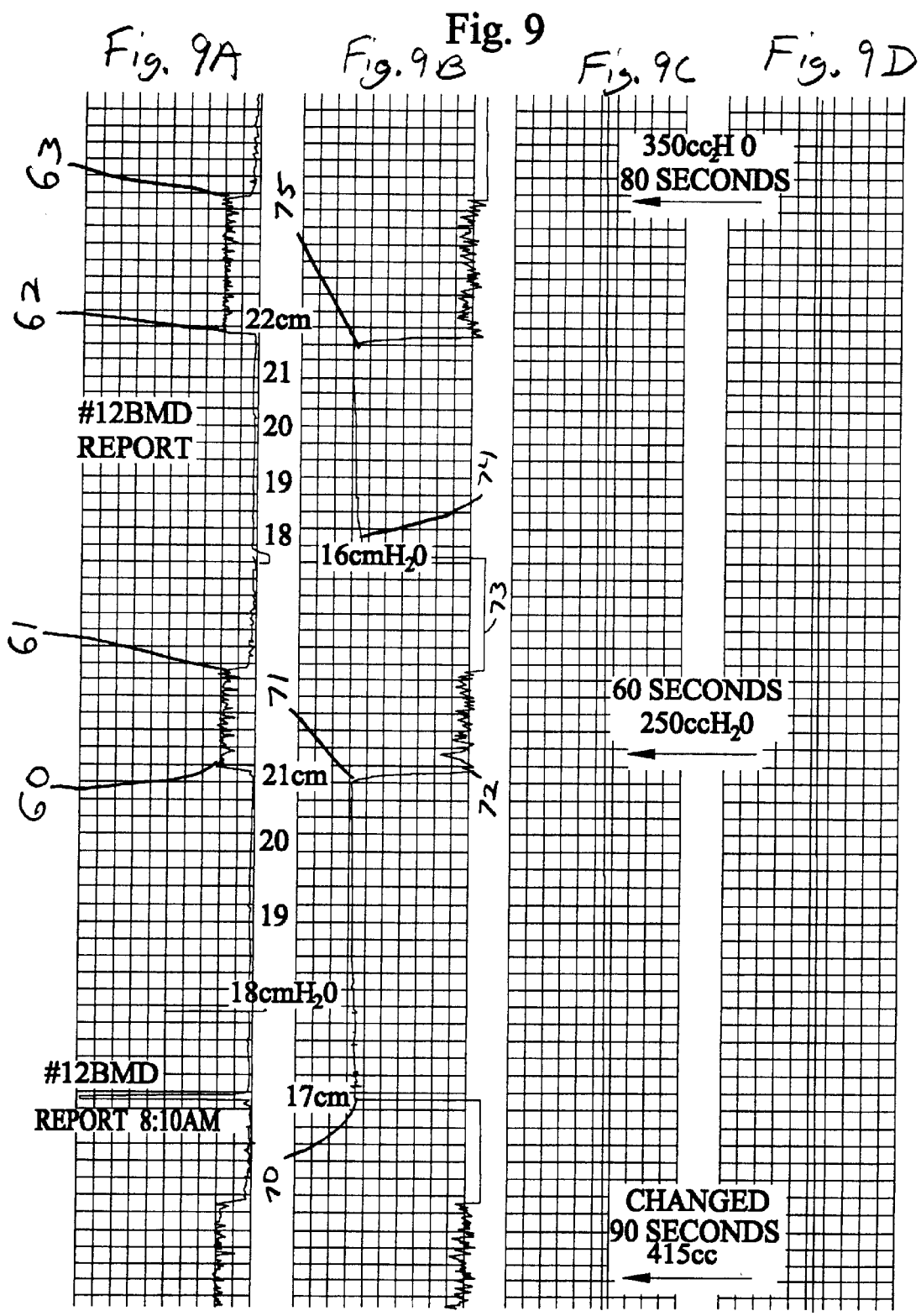
FIGS. 9A, 9B, 9C and 9D shows a fluid pressure and flow time chart showing the invention system operation.

In FIG. 9A, the commencement of urine flow is indicated at point 60. The flow is quite consistent throughout the time period ending at point 61, about 60 seconds. The flow charted from point 62 to 63 represents another bladder emptying cycle.

FIG. 9B illustrates the bladder pressure buildup cycle from 17 cm of water column pressure at point 70 to the valve opening threshold pressure of 21 cm at point 71, dropping to zero at point 72. At point 73, the chart stops and a new partial cycle from point 74 at 16 cm of H2O to the opening point 75 at 22 cm of H2O.

FIGS. 9C and 9D shows charts that indicate that the flow rates and urine volumes are in the "normal" range(e.g. approximately 250 cc over 60 minutes.

Referring to FIG. 7A a manual override embodiment can allow for selectively keeping valve 8 in an open position. For example, an extra outside magnet 50 can be positioned adjacent filter 6 to have South pole S, that attracts North pole N, of moving valve 8 in an open position. The manual override of the valve can occur by selective distancing of an externally positioned magnetic 50 from the valve 8 that is attracted to it. The override gives flexibility of pressure adjustment and provides the opportunity of assuring full drainage when desired by either physician or the patient. This could manifest itself, in the event of excessive discharge of viscous matter or other mode of lumen blockage, as a welcome "safety" valve to relieve fluid pressure buildup in the line and system upstream from the cycler 1.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. A bladder cycler for use with catheters, comprising in combination:

a housing having an inlet end and an outlet end, connected to ends of a catheter;

means for interconnecting both the inlet end and the outlet end of the housing for allowing the housing to be held by the ends of the catheter;

a low pressure-activated valve inside the housing of the catheter, the valve having a first magnet which is stationary and a second magnet moveable relative to the first magnet, the second moveable magnet being moveable from a closed position to an open position, wherein low pressure applied to the pressure-activated valve allows for the valve to move from a closed position to inhibit fluid flow therethrough to an open position which allows the fluid flow therethrough; and an adjustably moveable third magnet fixably attached to the housing and being adjacent to the stationary first magnet, the third magnet for adjusting magnetic attraction forces between the first magnet and the second magnet.

2. The bladder cycler of claim 1, further comprising:

a longitudinal member being moveably protruding into the housing, the longitudinal member having one end external to the housing and an internal end with the third magnet, the longitudinal member being moveable at different increments in and out of the housing by the external end.

3. The bladder cycler of claim 2, wherein the longitudinal member includes:

threaded side portions for allowing the longitudinal member to be rotatably adjustable into and out of the housing.

4. A bladder cycler for use with catheters, comprising in combination:

a housing having an inlet end and an outlet end, connected to ends of a catheter;

means for interconnecting both the inlet end and the outlet end of the housing for allowing the housing to be held by the ends of the catheter;

a low pressure-activated valve inside the housing of the catheter, the valve having a first magnet which is stationary and a second magnet moveable relative to the first magnet, the second moveable magnet being moveable from a closed position to an open position, wherein low pressure applied to the pressure-activated valve allows for the valve to move from a closed position to inhibit fluid flow therethrough to an open position which allows the fluid flow therethrough; and a vent valve passing through the outlet end of the housing for aiding in drainage of the fluid through the housing the vent valve further having means for preventing moisture from forming within the housing and the catheter so that bacteria growth is prevented.

5. The bladder cycler of claim 4, further comprising:

an adjustably moveable third magnet fixably attached to the housing and being adjacent to the stationary first magnet, the third magnet for adjusting magnetic attraction forces between the first magnet and the second magnet.

6. The bladder cycler of claim 5, further comprising:

a longitudinal member being moveably protruding into the housing, the longitudinal member having one end external to the housing and an internal end with the third magnet, the longitudinal member being moveable at different increments in and out of the housing by the external end.

7. The bladder cycler of claim 6, wherein the longitudinal member includes:

threaded side portions for allowing the longitudinal member to be rotatably adjustable into and out of the housing.

8. The bladder cycler of claim 4, wherein the vent valve further includes:

means for holding the vent valve in an open position to aid in drainage of the fluid through the housing.

9. The bladder cycler of claim 4, wherein the vent valve further includes:

a filter covering the vent valve for allowing bubbles to enter downstream from the housing for aiding drainage of the fluid through the housing.

10. A bladder cycler for use with catheters, comprising in combination:

a housing having an inlet end and an outlet end, connected to ends of a catheter;

means for interconnecting both the inlet end and the outlet end of the housing for allowing the housing to be held by the ends of the catheter;

a low pressure-activated valve inside the housing of the catheter, the valve having a first magnet which is stationary and a second magnet moveable relative to the first magnet, the second moveable magnet being moveable from a closed position to an open position, wherein low pressure applied to the pressure-activated valve allows for the valve to move from a closed position to inhibit fluid flow therethrough to an open position which allows the fluid flow therethrough; and a vent valve passing through the outlet end of the housing for aiding in drainage of the fluid through the housing, the vent valve having a filter covering the vent valve for allowing bubbles to enter downstream from the housing for aiding drainage of the fluid through the housing.

11. The bladder cycler of claim 10, further comprising:

an adjustably moveable third magnet fixably attached to the housing and being adjacent to the stationary first magnet, the third magnet for adjusting magnetic attraction forces between the first magnet and the second magnet.

12. The bladder cycler of claim 11, further comprising:

a longitudinal member being moveably protruding into the housing, the longitudinal member having one end external to the housing and an internal end with the third magnet, the longitudinal member being moveable at different increments in and out of the housing by the external end.

13. The bladder cycler of claim 12, wherein the longitudinal member includes:

threaded side portions for allowing the longitudinal member to be rotatably adjustable into and out of the housing.

* * * * *